US012653413B2

(12) United States Patent　　　　　(10) Patent No.:　US 12,653,413 B2
Whitaker et al.　　　　　　　　　　　(45) Date of Patent:　Jun. 16, 2026

(54) LOW COST RESPIRATION SENSING USING MM WAVE RADAR

(71) Applicant: Welch Allyn, Inc., Skaneateles Falls, NY (US)

(72) Inventors: Tyson B. Whitaker, Arden, NC (US); Gene J. Wolfe, Pittsford, NY (US); John A. Lane, Weesport, NY (US); David E. Quinn, Auburn, NY (US); WonKyung McSweeney, Manlius, NY (US)

(73) Assignee: Welch Allyn, Inc., Skaneateles Falls, NY (US)

( * ) Notice:　Subject to any disclaimer, the term of this patent is extended or adjusted under 35 U.S.C. 154(b) by 0 days.

(21) Appl. No.: 18/774,984

(22) Filed:　Jul. 17, 2024

(65)　　　　Prior Publication Data

US 2025/0031989 A1　　Jan. 30, 2025

Related U.S. Application Data

(60) Provisional application No. 63/528,793, filed on Jul. 25, 2023.

(51) Int. Cl.
　　*A61B 5/0507*　　(2021.01)
　　*A61B 5/11*　　　(2006.01)
　　*A61B 5/113*　　　(2006.01)
(52) U.S. Cl.
　　CPC .......... *A61B 5/0507* (2013.01); *A61B 5/1114* (2013.01); *A61B 5/1135* (2013.01)
(58) Field of Classification Search
　　CPC ... A61B 5/1114; A61B 5/1135; A61B 5/0015; A61B 5/0816
　　See application file for complete search history.

(56)　　　　References Cited

U.S. PATENT DOCUMENTS 3,796,208　A　*　3/1974　Bloice ..................... G01S 13/50
　　　　　　　　　　　　　　　　　　　600/595
4,901,083　A　*　2/1990　May ...................... G01S 13/931
　　　　　　　　　　　　　　　　　　　342/128
(Continued)

FOREIGN PATENT DOCUMENTS

CN　　　113384250 A　　9/2021
CN　　　115024701 A　　9/2022
(Continued)

OTHER PUBLICATIONS

Yong [Remote Monitoring of Human Vital Signs Based on 77-GHz mm-Wave FMCW Radar, Sensors 2020, 20, 2999; doi: 10.3390/s20102999] (Year: 2020).*

*Primary Examiner* — Oommen Jacob
(74) *Attorney, Agent, or Firm* — Price Heneveld LLP

(57)　　　　ABSTRACT

A biological monitoring device, including a housing and a distance sensor in connection with the housing, where the distance sensor is configured to emit an electromagnetic wave into a local environment and to sense the electromagnetic wave reflected off an object in the local environment and within a detection field of the distance sensor. A controller is communicatively in connection with the distance sensor. The controller is configured to control the distance sensor to emit the electromagnetic wave, detect a change in distance between the biological monitoring device and the object based on the electromagnetic wave emitted by the distance sensor, and determine a rate of a periodic biological movement based on the change of distance.

20 Claims, 6 Drawing Sheets

(56) References Cited

U.S. PATENT DOCUMENTS

| | | | | |
|---|---|---|---|---|
| 5,134,411 | A * | 7/1992 | Adler | G01S 7/023 |
| | | | | 342/128 |
| 6,062,216 | A * | 5/2000 | Corn | G01S 17/50 |
| | | | | 128/204.23 |
| 8,454,528 | B2 * | 6/2013 | Yuen | A61B 5/113 |
| | | | | 600/407 |
| 9,638,519 | B2 * | 5/2017 | Kwiatkowski | G01C 1/04 |
| 9,750,429 | B1 * | 9/2017 | Sackner | A61B 5/6804 |
| 10,772,511 | B2 | 9/2020 | Sahin et al. | |
| 10,893,811 | B2 | 1/2021 | De Chazal et al. | |
| 11,278,241 | B2 | 3/2022 | Baheti et al. | |
| 11,412,937 | B2 | 8/2022 | Ahmad et al. | |
| 2002/0032386 | A1 * | 3/2002 | Sackner | A61B 5/1135 |
| | | | | 600/509 |
| 2007/0025738 | A1 * | 2/2007 | Moore | H04B 10/1149 |
| | | | | 398/189 |
| 2008/0077020 | A1 * | 3/2008 | Young | A61B 5/746 |
| | | | | 73/726 |

| | | | | |
|---|---|---|---|---|
| 2009/0315761 | A1 * | 12/2009 | Walter | G01S 13/931 |
| | | | | 342/200 |
| 2010/0152600 | A1 * | 6/2010 | Droitcour | A61B 5/7221 |
| | | | | 600/534 |
| 2014/0350428 | A1 | 11/2014 | Kasama | |
| 2019/0069840 | A1 * | 3/2019 | Young | A61F 5/56 |
| 2020/0237252 | A1 | 7/2020 | Lane et al. | |
| 2020/0260998 | A1 | 8/2020 | Auerbach et al. | |
| 2020/0330068 | A1 * | 10/2020 | Mudge | A61B 8/5223 |
| 2022/0296111 | A1 | 9/2022 | Leabman | |
| 2022/0296165 | A1 | 9/2022 | Datta et al. | |
| 2022/0299628 | A1 | 9/2022 | Chang et al. | |
| 2022/0346653 | A1 | 11/2022 | Teng et al. | |
| 2025/0031989 | A1 * | 1/2025 | Whitaker | A61B 5/0507 |

FOREIGN PATENT DOCUMENTS

| | | | | | |
|---|---|---|---|---|---|
| GB | | 2116725 | B * | 7/1985 | A61B 5/1135 |
| WO | WO-2021229250 | A1 * | 11/2021 | | A61M 16/00 |

* cited by examiner

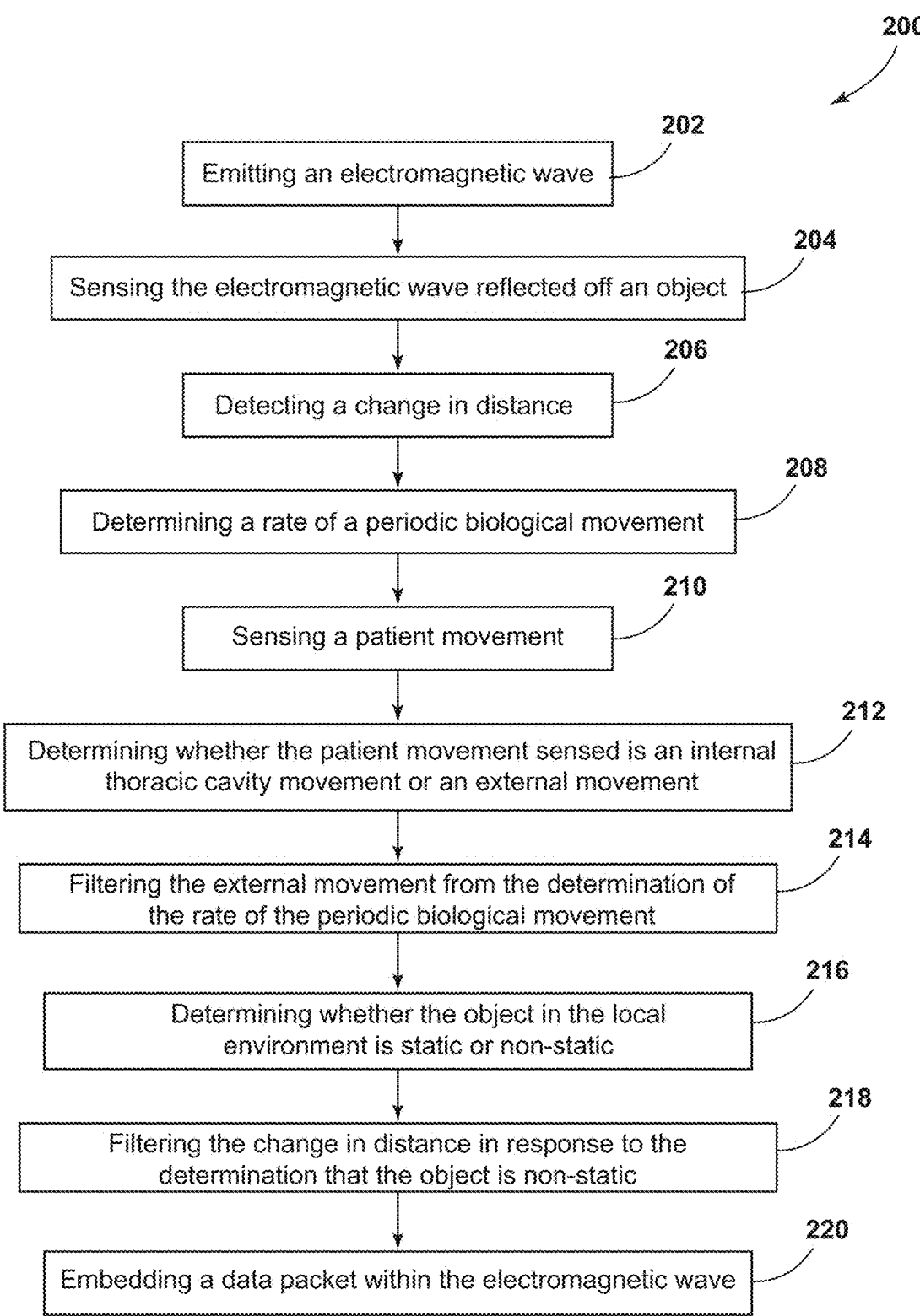

200

202
Emitting an electromagnetic wave

204
Sensing the electromagnetic wave reflected off an object

206
Detecting a change in distance

208
Determining a rate of a periodic biological movement

210
Sensing a patient movement

212
Determining whether the patient movement sensed is an internal thoracic cavity movement or an external movement 214
Filtering the external movement from the determination of the rate of the periodic biological movement 216
Determining whether the object in the local environment is static or non-static 218
Filtering the change in distance in response to the determination that the object is non-static 220
Embedding a data packet within the electromagnetic wave

FIG. 6

LOW COST RESPIRATION SENSING USING MM WAVE RADAR

CROSS-REFERENCE TO RELATED APPLICATIONS

This application claims priority under 35 U.S.C. § 119(e) and the benefit of U.S. Provisional Application No. 63/528, 793 entitled Low COST RESPIRATION SENSING USING MM WAVE RADAR, filed on Jul. 25, 2023, by Tyson B. Whitaker, et al., the entire disclosure of which is incorporated herein by reference.

BACKGROUND OF THE INVENTION

The present invention relates to a wearable biological monitoring device and, more particularly, a wearable biological monitoring device configured to sense a rate of a periodic biological movement of a user.

SUMMARY OF THE INVENTION

According to one aspect of the present disclosure, a biological monitoring device, including a housing and a distance sensor in connection with the housing, is disclosed. The distance sensor is configured to emit an electromagnetic wave into a local environment and to sense the electromagnetic wave reflected off an object in the local environment and within a detection field of the distance sensor. A controller is communicatively in connection with the distance sensor. The controller is configured to control the distance sensor to emit the electromagnetic wave, detect a change in distance between the biological monitoring device and the object based on the electromagnetic wave emitted by the distance sensor, and determine a rate of a periodic biological movement based on the change in distance.

According to another aspect of the present disclosure, a method for monitoring a periodic biological movement, including emitting an electromagnetic wave into a local environment and sensing the electromagnetic wave reflected off an object located in the local environment, is disclosed. The method further includes detecting a change in distance between an origin of the electromagnetic wave and the object in the located environment based on the electromagnetic wave. A rate of the periodic biological movement is determined based on the change in distance between the biological monitor and the object.

According to yet another aspect of the present disclosure, a patient monitoring system comprises a housing and a distance sensor in connection with the housing. The distance sensor is configured to emit an electromagnetic wave into a local environment and to sense the electromagnetic wave reflected off an object in the local environment within a detection field of the distance sensor. A first controller is communicatively in connection with the distance sensor. The first controller is configured to control the distance sensor to emit the electromagnetic wave and detect a change in distance between the distance sensor and the object based on the electromagnetic wave emitted by the distance sensor. The controller further determines a rate of a periodic biological movement based on the change of distance and transmits a data packet to a second controller separate from the housing.

These and other features, objects and advantages of the present invention will become apparent upon reading the following description thereof together with reference to the accompanying drawings.

BRIEF DESCRIPTION OF THE DRAWINGS

FIG. 6 is a flow diagram of a method of determining a rate of a periodic biological movement according to the present disclosure.

DETAILED DESCRIPTION OF THE PREFERRED EMBODIMENT

Figure 3:
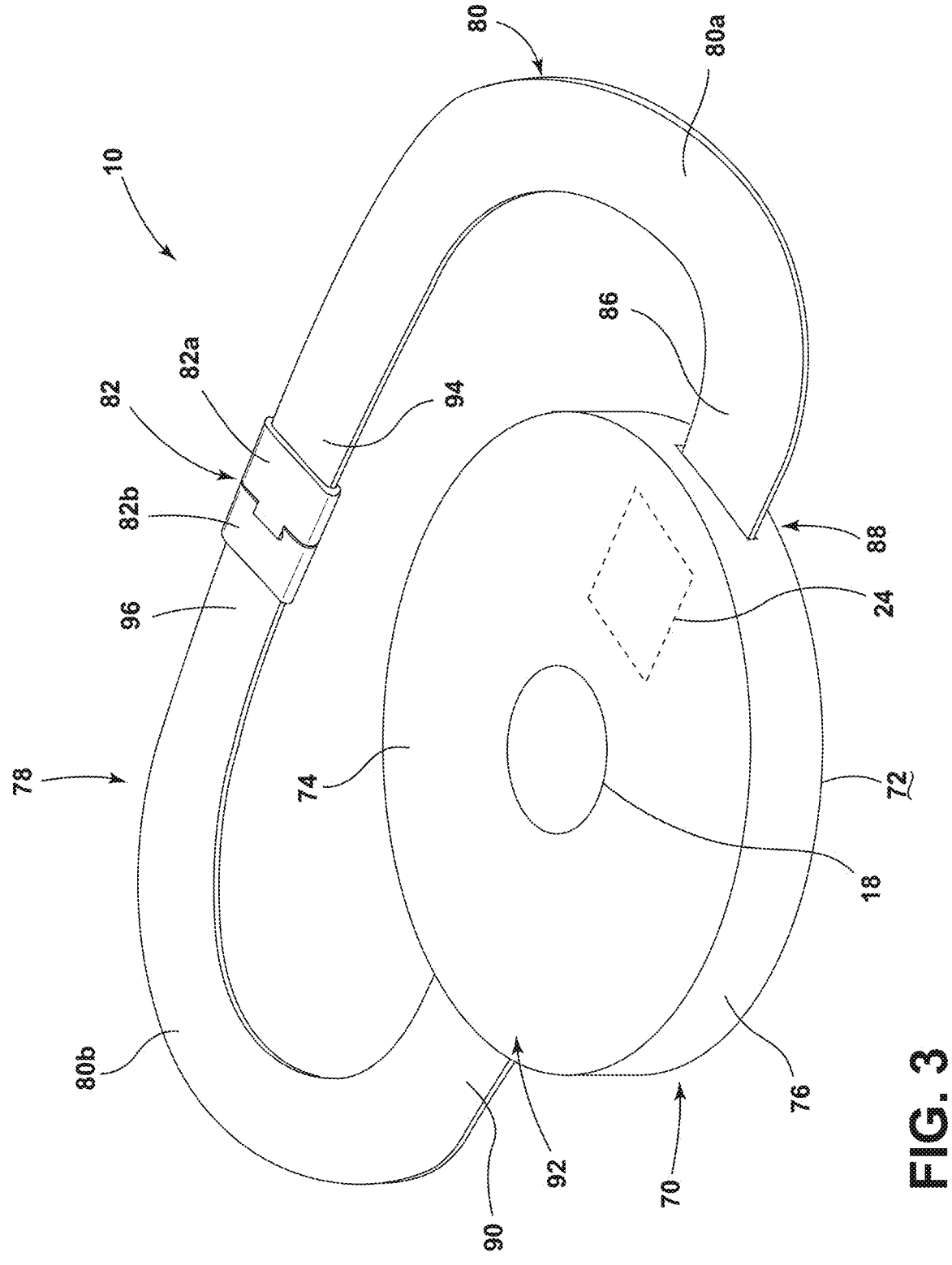
FIG. 3 is a schematic perspective view of a biological monitoring device.

For purposes of description herein, the terms "upper," "lower," "right," "left," "rear," "front," "vertical," "horizontal," and derivatives thereof shall relate to the invention as oriented in FIG. 3. Unless stated otherwise, the term "front" shall refer to the surface of the element facing away from an intended user, and the term "rear" shall refer to the surface of the element proximate or facing toward the intended user. However, it is to be understood that the invention may assume various alternative orientations, except where expressly specified to the contrary. It is also to be understood that the specific devices and processes illustrated in the attached drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-4, the disclosure provides a biological monitoring device 10 for monitoring a rate of a periodic biological movement 12, such as a heart rate or a respiration rate, of a user or patient 14. The biological monitoring device 10 may be attached to the user 14 and positioned over or proximate a patient cavity 16 (e.g., thoracic cavity, abdomen, etc.) of the user 14 to capture the rate of the periodic biological movement 12. Generally, the monitoring device 10 may detect motion of the user 14 with a distance sensor 18. The distance sensor 18 may be configured to detect a distance between the monitoring device 10 and an object 20 in a local environment 22 of the user 14. The monitoring device 10 may include a controller 24 configured to determine the rate of the periodic biological movement 12. The controller 24 may be in communication with the distance sensor 18 and configured to control the distance sensor 18. The distance sensed by the distance sensor 18 may be used to detect a change in distance between the biological monitoring device 10 and the object 20. As provided in various examples in the following disclosure, the change in distance may be monitored and analyzed over time to determine the rate of the periodic biological movement 12 of the user 14.

In some implementations, the controller 24 may distinguish periodic biological movements associated with the movement of the patient cavity 16 from other motions associated with changes in the position of the monitoring device 10. For example, the periodic biological movement 12 of the user caused by an internal thoracic movement may be distinguished from positional changes that may result from other movements (e.g., locomotion of one or more portions of the body) of the user or the object 20. For example, the controller 24 may filter or omit results that do not correspond to the internal biological movements 12 and instead correspond to other movements that may be attributed to speaking, walking, changing physical positions, etc. Similarly, the controller 24 may distinguish signals reflected from moving objects as opposed to stationary or temporarily static objects that may be referenced to accurately detect the movement of the monitoring device 10 responsive to the internal biological movement 12. In this way, the system may accurately track internal thoracic and/or abdominal movements of the user 14 (e.g., movements effectuated by respiration or a pulse of the user 14) to provide various benefits.

Figure 1:
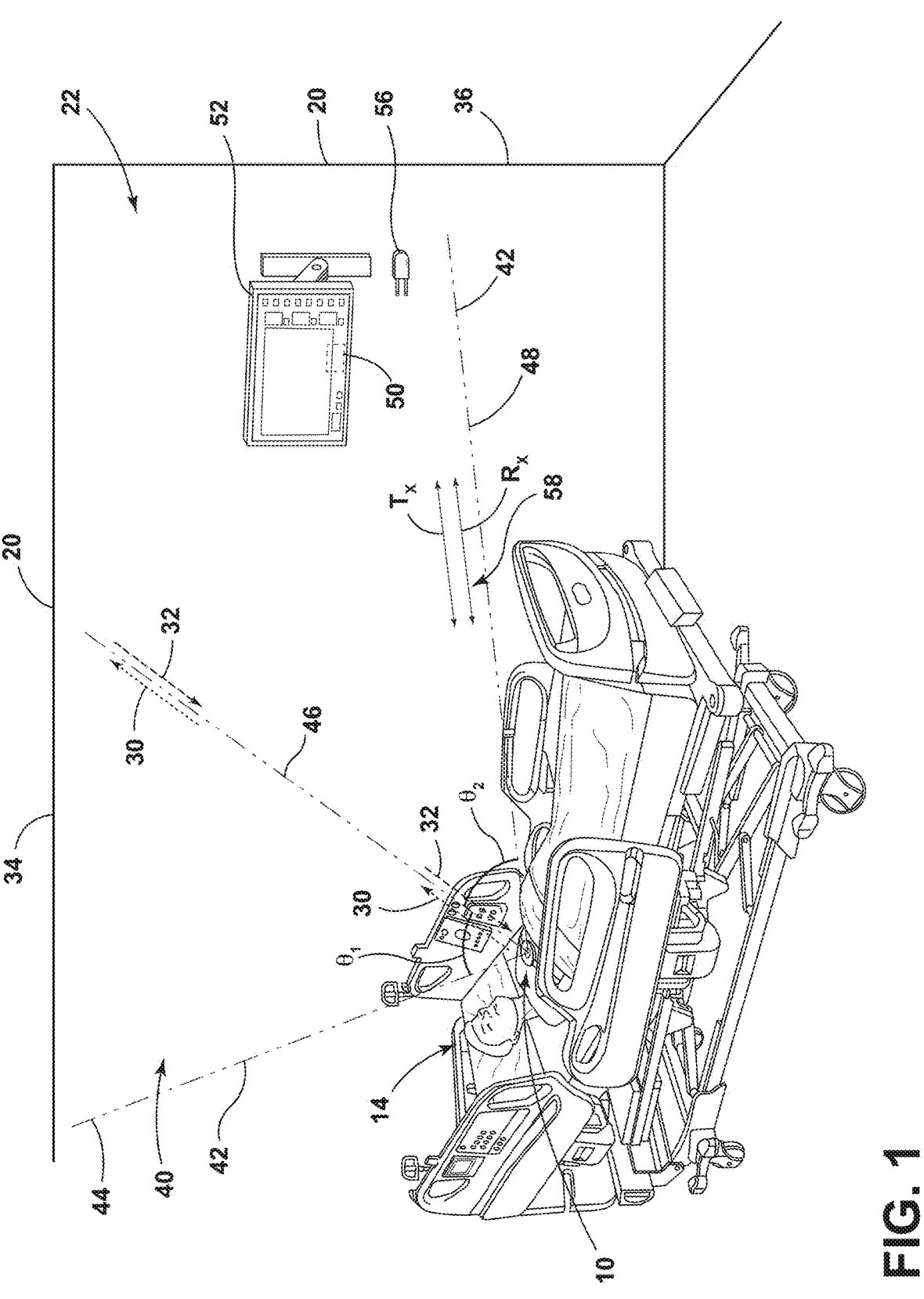
FIG. 1 is a schematic diagram of a healthcare room including a patient and a biological monitoring device.
Figure 2:
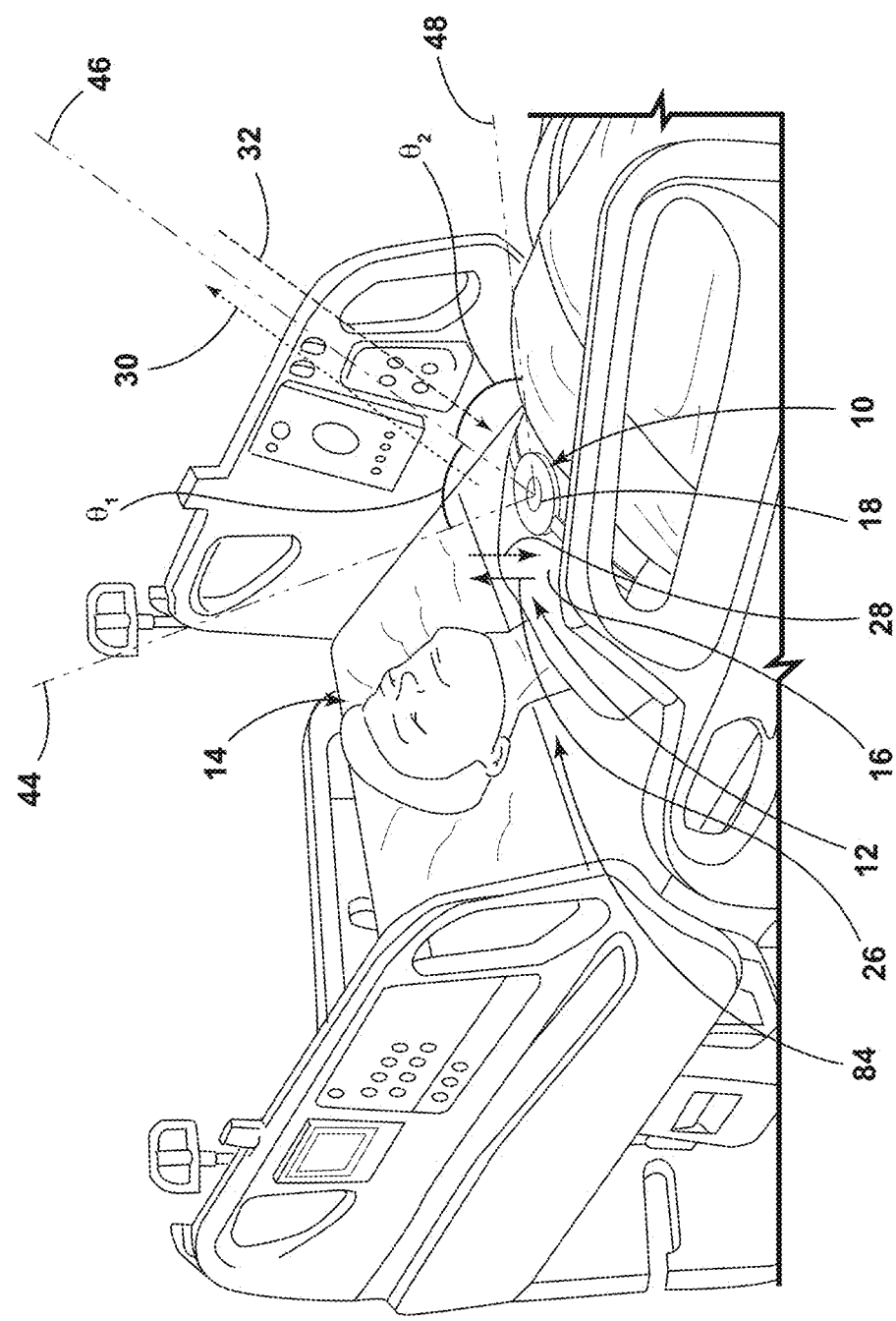
FIG. 2 is a schematic diagram of a patient and a biological monitoring device in a healthcare setting.

Referring to FIGS. 1 and 2, the biological monitoring device 10 is shown in connection with or otherwise coupled to the user 14 proximate the patient cavity 16. The user 14 is illustrated as laying in a bed, but the monitoring device 10 may be used with the user 14 in other positions, such as sitting in a chair. As respiration and pulses of the heart of the user 14 occur, the relative position of the patient cavity 16 varies in position relative to one or more stationary surfaces or objects 20 in the local environment 22. In the example of the patient 14 in the supine position, the position of the chest or patient cavity 16 rises, as shown by arrow 26, and falls, as shown by arrow 28. More generally, the periodic changes in position of the biological monitoring device 10 (e.g., the rises 26 and falls 28) vary with the movement of the patient cavity 16, thus changing the distance between the distance sensor 18 and the object 20.

Generally, as illustrated in FIG. 1, the controller 24 of the monitoring device 10 may monitor signals reported by one or more sensors including the distance sensor 18 to monitor various vital signs, movements, and/or various conditions attributed to the patient 14 and the local environment 22. Throughout a monitoring operation, the controller 24 may initiate and control the distance sensor 18 to emit an electromagnetic wave into the local environment 22, as shown by arrows 30. In response to sensor data reported by the distance sensor 18, the controller 24 may determine the distance between the distance sensor 18 and the object 20. In various implementations, the controller 24 may be configured to instruct the distance sensor 18 to emit the electromagnetic wave pattern or signal, such that the controller 24 may determine the change in distance between the distance sensor 18 and the object 20. In operation, the emitted electromagnetic wave 30 travels through the local environment 22 until the wave is reflected off the object 20 in the local environment 22. The object 20 from which the emitted electromagnetic wave 30 is reflected may include various objects in the local environment 22. For example, the object 20 may correspond to a ceiling 34 or walls 36 of the local environment 22, equipment designed to reflect the electromagnetic wave 30, or other objects within a field of detection 40 of the distance sensor 18.

As shown in FIGS. 1 and 2, the reflected electromagnetic wave, illustrated as arrows 32, may travel from the object 20, through the local environment 22, and be detected as returning to the distance sensor 18 by a receiver or antenna that may be tuned to a frequency of the electromagnetic wave 32. In order to calculate a distance from the device 10 to the object 20, in operation, the controller 24 may calculate a time-of-flight or signal change between the emitted electromagnetic wave 30 and the reflected electromagnetic wave 32 sensed by the distance sensor 18 to infer the distance between the monitoring device 10 and the object 20. Over time, changes in the distance may be tracked to determine or estimate the movement attributed to the internal biological movement 12 to determine corresponding rate information (e.g., respiration rate, pulse rate, etc.).

As previously described, the movements of the device 10 may be attributed to various forms of motion. For example, the controller 24 may use the change in distance between the monitoring device 10 and the object 20 to determine the rate of the periodic biological movement 12. However, the controller 24 may similarly detect movements that are periodic or sporadic. In order to accurately detect the movement corresponding to vital signs or other biological movements 12, the controller 24 may filter from the determination of the rate of the periodic biological movement 12 the change in distance caused by movement of the user that is not an internal thoracic movement. The controller 24 may also filter the change in distance caused by the object moving from the determination of the rate of the periodic biological movement 12. The controller 24 may also be configured to determine whether the object 20 in the local environment 22 is static or non-static based on the change in distance between the biological monitoring device 10 and the object 20.

The recorded variations in the position of the device 10 and the distance sensor 18 over time may be filtered based on expected ranges and frequencies that are characteristic of the corresponding biological events tracked by the device 10. For example, the periodic biological movement 12 may be distinguished from other movements of the user 14 or object 20 based on one or more distance ranges, frequencies, or other characteristics detected by the device 10 and associated with the movement 12. In operation, the controller 24 may remove or filter values of the recorded change in distance from the determination of the rate of the vital sign or biological movement 12 based on the established distance range for the corresponding event (e.g., respiration). The expected range for change in distance for respiration may be between about 1 mm and about 20 mm. The expected range for change in distance for a heartbeat or pulse may be between about 0.01 mm and about 0.5 mm. For example, when the controller is determining a vital sign, such as a breathing rate, the controller will filter periods of detection that include changes in distance less than 1 mm and greater than 20 mm from the determination of the rate. In this way, non-conforming activity may be filtered from the distance information detected by the device 10.

The controller 24 may also remove or filter values of the recorded change in distance based on the activity conforming to a predetermined rate or range of rates of the biological movement 12 corresponding to an expected frequency of the rate of the vital sign or biological movement. For example, the controller 24 may process the distance data to identify a frequency of one or more periodic changes in the distance measurements identified by the distance sensor 18. The controller 24 may then filter or remove portions of the sensor data that correspond to frequencies outside a range attributed to the biological movement 12 (e.g., the respiration rate). In some cases, the controller may apply a band-pass filter to remove frequencies outside the established ranges for the vital signs of one or more periodic biological movements 12. The established range of frequency for heart rate may fall between about 0.5 Hz (about 30 beats per minute) and about 4 Hz (240 beats per minute). The established range of frequency for respiration rate may fall between about 0.07 Hz (4 breaths per minute) and about 0.47 Hz (28 breaths per minute). Accordingly, the controller 24 may use one or both the change in distance-based and the frequency-based filtering to improve the accuracy of the calculated rate associated with the biological movement 12.

As previously discussed, the distance sensor 18 may provide for a field of detection 40. As shown in FIG. 1, the field of detection 40 may correspond to a range extending to a boundary 42 over which an antenna or receiver of the distance sensor 18 is operable to detect the reflected electromagnetic waves and accurately determine the change in distance between the biological monitoring device 10 and the object 20. At present, distance sensors, such as mm wave sensors, may accurately detect variations of absolute distances at a measurement resolution of 5 μm with absolute accuracy of 25 μm. However, it shall be understood that other detection technologies and improvements may be associated with the accuracy or the distance sensor 18 may be implemented by the disclosure. As shown, the boundary 42 has a first side 44 extending at a first angle $\Theta_1$ relative to a reference line 46 of the field of detection 40 and a second side 48 extending at a second angle $\Theta_2$ relative to the reference line 46. The reference line 46 extends from a center point of the distance sensor 18 and is perpendicular to the distance sensor 18. In some embodiments, the first angle $\Theta_1$ may be substantially similar to the second angle $\Theta_2$. In other embodiments, the first angle $\Theta_1$ may be greater or smaller than the second angle $\Theta_2$.

In various configurations, the controller 24 may record the change in distance detected by the distance sensor 18 to internal memory. The distance sensor may continuously output the change in distance readings. The controller 24 may access recorded changes in distance to make the determination of rate for the periodic biological movement 12. The controller 24 may also store the rate of the biological movement 12 over a period of time to the internal memory. Other programming routines, data, and/or information associated with the operation of the device 10 and detected vital information for the patient 14 (e.g., temperature, vital data, etc.) may be stored by the controller 24 on the internal memory. The controller may access the stored data and transmit the information as data packets to a secondary controller 50.

The biological monitoring device 10 may communicate with the secondary controller 50, which may be included in a patient monitoring system 52, a remote patient data storage system, or other remote computer. The secondary controller 50 may be spatially separate or remotely located from the monitoring device 10. Thus, the secondary controller 50 may include or be in communication with a wireless communication module 56 to effectuate communication. The wireless communication module 56 may allow for the secondary controller 50 and the controller 24 to establish a wireless data connection 58. The wireless data connection 58 allows the controller 24 to transmit Tx data packets to and receive data packets Rx from the secondary controller 50. Similarly, the wireless data connection 58 allows for the secondary controller 50 to transmit Tx data packets to and receive Rx data packets from the controller 24. The data packets may include various data (e.g., vital information, patient data, etc.) attributed to the operation of the device 10 and/or the condition of the patient 14. For example, the data packets may include one or more rates of the periodic biological movement 12 determined by the controller 24. The data packets may also include calibration settings or software updates for the controller 24 or other devices coupled with the controller 24. The secondary controller 50 may be configured to record and store the received data packets from the biological monitoring device 10.

In various implementations, the wireless data connection 58 may be established using the distance sensor 18 to transmit the data packets to the wireless communication module 56 and/or to receive the data packets from the wireless communication module 56. The distance sensor 18 may emit electromagnetic waves that contain the data packets that can be received by the wireless communication module 56. As shall be understood, the wireless communication module 56 may not have to be located within the field of detection 40 of the distance sensor 18 to maintain communication with the device 10, as the distance sensor 18 may emit electromagnetic signals containing the data packets outside the field of detection 40. Stated differently, the emission range of the emitter of the distance sensor 18 may not be limited to the field of detection 40. The distance sensor 18 may also be used to receive data packets transmitted by the wireless communication module 56 through an emitted electromagnetic wave including the data packets. The distance sensor 18 may receive the data packets from the emitted electromagnetic wave even when the origin of the electromagnetic wave from the wireless communication module 56 is outside the field of detection 40. The distance sensor 18 may have a larger field of detection for sensing the electromagnetic wave and receiving the data packets emitted by the communication module 56 because the detection of the distance is not dependent on such communications. Thus, the distance sensor 18 and communication module 56 may be used to establish communication between the controller 24 and the secondary controller 50 and allow for data packets to be transmitted therebetween.

Referring to FIG. 3, the monitoring device 10 may include a housing 70 configured to be worn by the user 14. As illustrated, the housing 70 defines a user-facing surface 72, an outer surface 74, and a side surface 76 that extends around a perimeter of the housing 70. The housing 70 has a generally circular perimeter, however, the housing 70 is not limited to such a perimeter. The housing 70 may have, for example, an ovoid, a rectangular, or other perimeter shape. The housing 70 may include the distance sensor 18 coupled to or integrated with the outer surface 74 of the housing. This configuration allows for the distance sensor 18 to emit the electromagnetic waves into the local environment 22 and away from the user 14 when the monitoring device 10 is worn by the user 14. The user-facing surface 72 opposes the outer surface 74 of the housing 70 and is proximate to the user 14 in this configuration. The housing 70 may also define an internal volume where the controller 24 and other sensor or components may be disposed.

The monitoring device 10 may include a coupling device 78 to couple the housing 70 to the user 14. As illustrated in FIGS. 2 and 3, the coupling device 78 is a strap 80 with a buckle assembly 82 that wraps around an upper body 84 of the user 14. The strap 80 may be a continuous single strap or split into strap segments. As illustrated, the strap 80 has a first strap segment 80a and a second strap segment 80b. A first end 86 of the first strap segment 80a may be coupled to the side surface 76 on a first side 88 of the housing 70. A first end 90 of the second strap segment 80*b* may be coupled to the side surface 76 of the housing 70 on a second end 92 of the housing 70. The first and second strap segments 80*a*, 80*b* may be coupled to other surfaces of the housing 70. The first and second strap segments 80*a*, 80*b* may generally be coupled to the housing 70 on opposing sides but is not limited to such configuration.

The buckle assembly 82 may have a first buckle 82*a* and a second buckle 82*b*. As illustrated in FIG. 3, the first buckle 82*a* is coupled to a second end 94 of the first strap segment 80*a*. The second buckle 82*b* is coupled to a second end 96 of the second strap segment 80*b*. The first buckle 82*a* and the second buckle 82*b* are configured to selectively couple and uncouple with one another. When the first buckle 82*a* and second buckle 82*b* are coupled together, the strap 80, the buckle assembly 82, and the housing 70 form a continuous loop that may be wrapped around the upper body 84 of the user 14 to couple the monitoring device 10 to the user. When the first buckle 82*a* and the second buckle 82*b* are uncoupled, the continuous loop is broken, allowing the monitoring device 10 to be removed from the user 14 or placed on the user 14.

The coupling device 78 may be coupled directly to the user 14 or coupled to clothing or outerwear of the user 14. The coupling device 78 is not limited to the strap 80 and buckle assembly 82 and may be an elastic strap, a pin, an adjustable strap, a clip, a shirt, magnets, adhesives, or other means to couple the monitoring device 10 to the user 14. For example, an elastic strap may be used as the coupling device 78 and stretched around the torso of the user 14 over the internal cavity 16. The elastic strap may apply a compression force pulling the monitoring device 10 toward the user 14, thus securing the device over the patient cavity 16. The elastic strap may allow for the device to be directly secured to the user 14 or placed over outerwear or clothing of the user 14. In another example, the coupling device 78 may be a skin-safe adhesive allowing the monitoring device 10 to be coupled over the patient cavity 16 and directly to the user 14. In this way, the coupling device 78 may allow for the device 10 to be coupled directly or indirectly over the patient cavity 16 of the user 14, thereby allowing the device 10 to detect the movement of the patient cavity 16.

Figure 4:
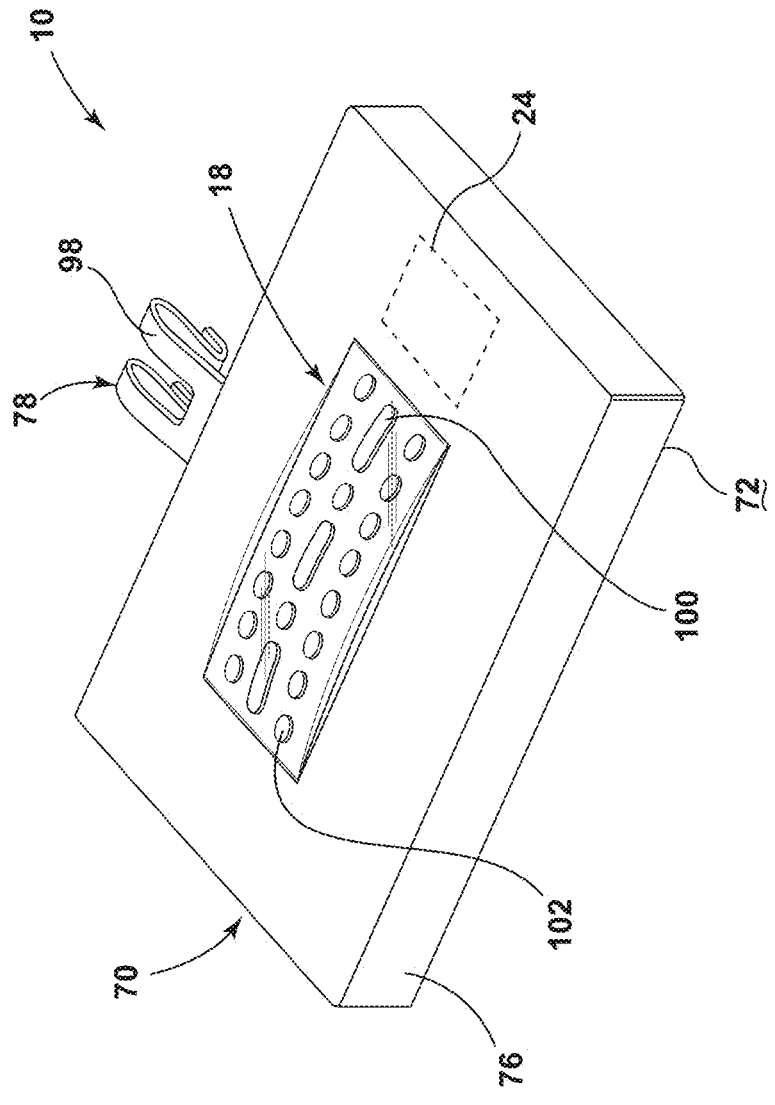
FIG. 4 is a schematic perspective view of a biological monitoring device having a phased array.

Referring to FIG. 4, the biological monitoring device 10 includes the housing 70, the coupling device 78, and the distance sensor 18. The housing 70 includes the user-facing surface 72, the outer surface 74, and the side surface 76. The housing 70 has a generally rectangular perimeter. The coupling device 78 is a clip 98 configured to allow attachment of the monitoring device 10 to clothing or garments worn by the user 14. The clip 98 allows for the biological monitoring device 10 to be selectively coupled to the user 14. The distance sensor 18 is coupled to the outer surface 74 of the biological monitoring device 10. The distance sensor 18 is depicted as a phased array that includes a plurality of emitter elements or transmitter elements 100 configured to emit the electromagnetic wave 30 and a plurality of sensor elements 102, where each sensor element of the plurality of sensor elements 102 is configured to sense the reflected electromagnetic wave 32. The phased array may include at least one transmitter element 100 and the plurality of sensor elements 102.

Referring again to both FIGS. 3 and 4, the controller 24 is configured to determine the change in distance between the distance sensor 18 and the object 20 in the local environment 22. The distance sensor 18 emits the electromagnetic wave 30 and senses the reflected electromagnetic wave 32. The distance sensor 18 may be a mm wave radar sensor, an IR distance sensor, a laser distance sensor (LIDAR), a light emitting diode (LED) time-of-flight distance sensor, or other time-of-flight sensors. The electromagnetic wave may have a millimeter (mm) wavelength between about 1 mm (30 GHz) and 10 mm (300 GHz) when the distance sensor 18 is a mm wave radar sensor.

The distance sensor 18 may also be a phased array including the plurality of emitter elements 100 and the plurality of sensor elements 102, as illustrated in FIG. 4. The plurality of emitter elements 100 may emit an electromagnetic wave having the same wavelength or having different wavelengths. Each sensor element of the plurality of sensor elements 102 may be configured to sense one wavelength of the electromagnetic wave or sense a plurality of wavelengths of electromagnetic waves. Each sensor element of the plurality of sensor elements 102 may have a sensor element field of detection corresponding to a portion or a segment of the field of detection 40. The sensor element segments of the field of detection 40 may overlap, allowing multiple sensor elements of the plurality of sensor elements 102 to detect a reflected electromagnetic wave in the same region of the field of detection 40. In operation, the phased array may output a plurality of distance signals that may be temporally sequenced or include characteristic frequencies or attributes allowing the controller 24 to distinguish activity in specific regions or segments of the field of detection 40. The controller 24 may be configured to track variations of distance signals corresponding to each of the regions over time to determine or estimate the movement attributed to the internal biological movement 12 used to determine corresponding rate information.

The controller 24 may be configured to compare the variations of distance signals corresponding to specific regions of the field of detection 40 to more accurately distinguish between movements corresponding to the periodic biological movement 12 or to other movements of the user 14 or the object 20. The controller 24 may isolate or filter changes in distance from a specific region when that change in distance has a large variation, indicating an outlier or error, compared to change in distance from other specific regions of the field of detection 40 over the same period. Outliers may be caused by movement of the user 14, movement of the object 20, or other causes, such as electrical interference. The controller 24 may determine when the change in distance is caused by movement of the object 20 verses a movement of the user 14 when the change in distance over a period across the regions of the field of detection 40 has minimal variation except for a specific region or multiple adjacent regions where the change in distance varies from the other regions. The controller 24 may filter or suppress data representative of outlying changes in distance determined not to be characteristic of the biological movement 12 and attributed to movement of the object 20. The recorded changes in distance of each segment of the field of detection 40 may be filtered based on expected ranges and frequencies that recur over time in order to accurately distinguish between movements corresponding to the periodic biological movement 12 or to other movements of the user 14 or the object, as discussed previously.

Figure 5:
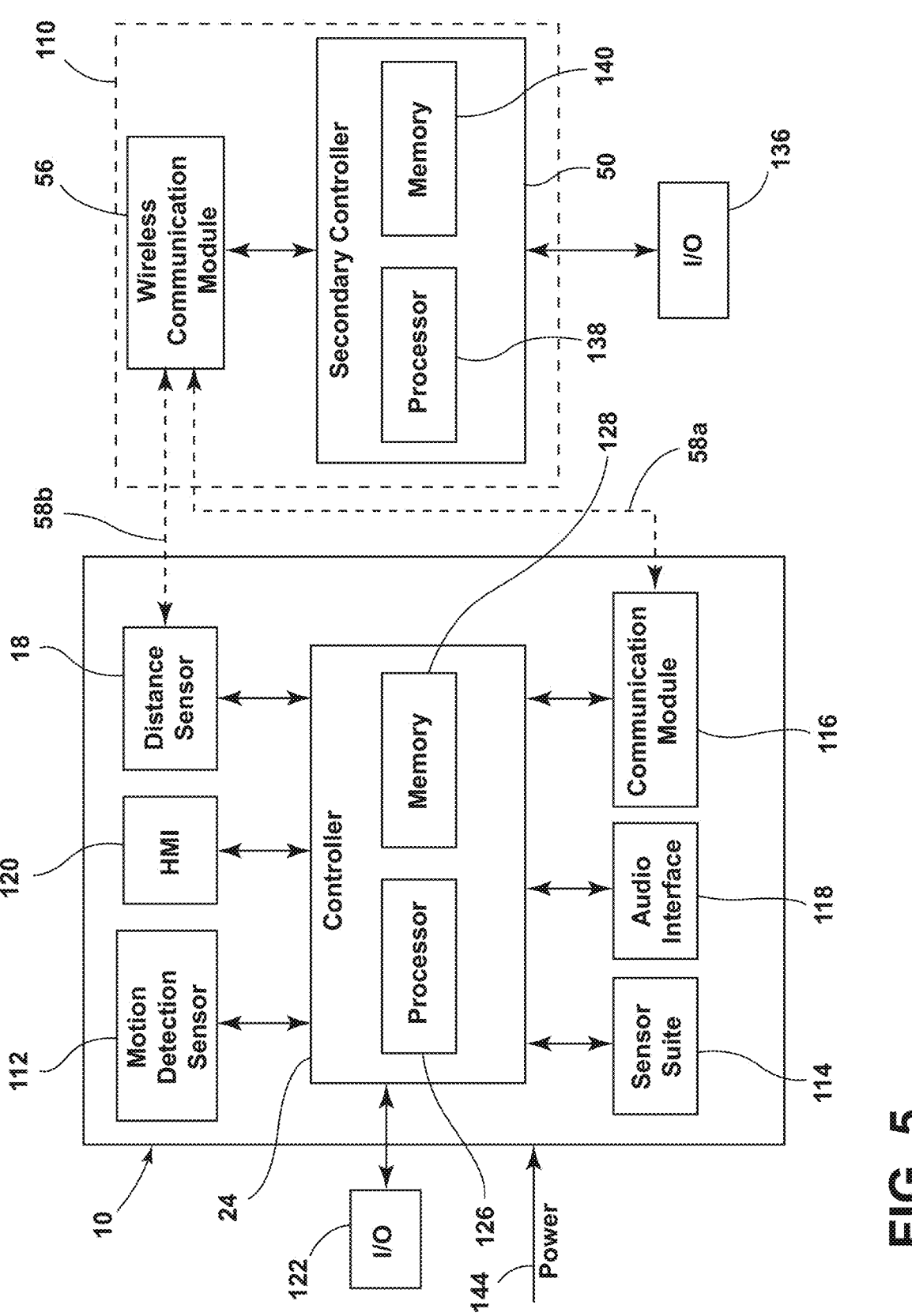
FIG. 5 is a block diagram of a biological monitoring device in communication with a secondary controller.

Referring to FIG. 5, a block diagram depicting an exemplary implementation of the biological monitoring device 10 communicatively coupled to the secondary controller 50 is shown. The controller 24 is shown in communication with the distance sensor 18. The controller 24 may also be in communication with a motion detection sensor 112, a sensor suite 114, a communication module 116, an audio interface 118, and/or a human machine interface (HMI) that may be integrated within the biological monitoring device 10. The controller 24 may also be in communication with various input/output (I/O) devices 122. The I/O devices 122 may include other vital measurement equipment, such as a blood pressure cuff, a blood oxygen sensor, or other sensors to monitor the user 14 or the user's movement, a wired data connection to the secondary controller 50, or other controllers or computer systems to interface with the controller 24 or the secondary controller 50 through the wireless data connection 58, as discussed below.

The controller 24 may comprise one or more processors 126 and a memory 128 or memory devices. The processor 126 may have one or more circuits configured to receive the signals from the distance sensor 18 and control the biological monitoring device 10. The processor 126 may have one or more circuits configured to control the motion detection sensor 112, the sensor suite 114, the communication module 116, and/or the I/O devices 122. The processor 126 may be in communication with the memory 128 configured to store instructions and/or algorithms to control operation of the biological monitoring device 10 in response to various inputs. For example, the inputs may include the emitted electromagnetic wave 30 and reflected electromagnetic wave 32 from the distance sensor 18. The memory 128 may comprise various forms of data or instruction storing technologies, including volatile and/or non-volatile memory that may include read-only memory (ROM), erasable/programmable read-only memory (EPROM), electronically erasable/programmable ROM (EEPROM), random access memory (RAM), etc. In operation, the memory 128 may store program instructions and routines that may be followed by the processor 126 to determine the rate of the periodic biological movement 12 in response to the emitted electromagnetic wave 30 and received electromagnetic wave 32 from the distance sensor 18.

The secondary controller 50 may be integrated with a patient monitoring system 110, which may include the local patient monitoring system 52 and/or the remote patient data system. The secondary controller 50 may be in communication with the wireless communication module 56. The secondary controller 50 may also be in communication with various input/output devices (I/O devices) 136. The I/O devices 136 may include data storage systems, display devices, sensors to detect other medical or vital signs of the user 14, various human machine interface implements (e.g., keyboard and mouse) and/or alarm or alert systems. The secondary controller 50 may comprise one or more processors 138 and a memory 140 or memory devices. The processor 138 may have one or more circuits configured to control the wireless communication module 56 and/or the I/O devices 136. The processor 138 may be in communication with the memory 140 configured to store instructions and/or algorithms to control operation of the patient monitoring system 52, the remote patient data storage system, and/or other computer systems. For example, the processor 138 may be configured to store a data packet received in a patient medical file in the memory 140 and/or the remote data storage system.

The memory 140 may comprise various forms of data or instruction storing technologies, including volatile and/or non-volatile memory that may include read-only memory (ROM), erasable/programmable read-only memory (EPROM), electronically erasable/programmable ROM (EEPROM), random access memory (RAM), etc. In operation, the memory 140 may store program instructions and routines that may be followed by the processor 138, such as data storage protocols or display routines to display the periodic biological movement on the display device. For example, the memory 140 may store a range of rates of the periodic biological movement. The processor 138 may be configured to monitor the rate of the periodic biological movement determined by the controller 24 and transmitted to the secondary controller 50. The processor 138 may be configured to activate an alarm or alert system when the rate of the periodic biological movement falls outside the range stored in the memory 140.

In various implementations, the controller 24 may be in communication with the patient monitoring system 110 with wireless data connections 58. A first wireless data connection 58a between the controller 24 and the secondary controller 50 may be established with the communication module 116 and the wireless communication module 56, shown in communication with the secondary controller 50 (FIG. 5). A second wireless data connection 58b between the controller 24 and the secondary controller 50 may be established with the distance sensor 18 and the wireless communication module 56. The wireless data connection 58 may be established using only the first wireless data connection 58a, using only the second wireless data connection 58b, or using both the first and second wireless data connections 58a, 58b. In some implementations, the communication module 116 is not in communication with the controller 24 or is not used to establish the wireless data connection 58 between the controller 24 and the secondary controller 50. In such implementations, only the second wireless data connection 58b using the distance sensor 18 can establish the wireless data connection 58 between the controller 24 and the secondary controller 50. The wireless data connection allows for the controller 24 and the secondary controller 50 to communicate and transmit data packets therebetween. The data packets may include information collected by the biological monitoring device 10 or received from the I/O devices 122 in communication with the biological monitoring device 10. The data packets may also include information stored on the secondary controller 50 or the I/O devices 136 in communication with the secondary controller 50.

In implementations where the first wireless data connection 58a is used for transmission of data packets between the controller 24 and the secondary controller 50, the controller 24 is configured to control the communication module 116. The communication module 116 may be configured to communicate via various mobile communication protocols. Wireless communication protocols may operate in accordance with communication standards including, but not limited to: Institute of Electrical and Electronic Engineering (IEEE) 802.11 (e.g., Wi-Fi®); Bluetooth®; advanced mobile phone services (AMPS); digital AMPS; global system for mobile communications (GSM); code division multiple access (CDMA); Long Term Evolution (LTE or 4G LTE); local multi-point distribution systems (LMDS); multi-channel-multi-point distribution systems (MMDS); radio frequency identification RFID; and/or variations thereof. The various mobile communications protocols generally use repeated waveforms to transmit information or data. In this configuration, the controller 24 may be configured to send data packets containing the rate of the periodic biological movement 12 or other data collected, stored, or sent to the controller 24. The controller 24 may also be configured to receive data packets containing information or programs, that may be used to update the controller 24 configuration, stored on the memory devices 128, calibrate the distance sensor 18, the motion detection sensor 112, the sensor suite 114, the I/O devices 122, and/or to transmit the data to the I/O devices 122.

Similarly, in implementations where the first wireless data connection 58*a* is used for transmission of data packets between the controller 24 and the secondary controller 50, the secondary controller 50 is configured to control the wireless communication module 56. The wireless communication module 56 may be configured to communicate via various mobile communication protocols. The wireless communication module 56 may be configured to communicate via the same mobile communication protocol as the communication module 116. Wireless communication protocols may operate in accordance with communication standards including, but not limited to: Institute of Electrical and Electronic Engineering (IEEE) 802.11 (e.g., Wi-Fi®); Bluetooth®; advanced mobile phone services (AMPS); digital AMPS; global system for mobile communications (GSM); code division multiple access (CDMA); Long Term Evolution (LTE or 4G LTE); local multi-point distribution systems (LMDS); multi-channel-multi-point distribution systems (MMDS); radio frequency identification RFID; and/or variations thereof. In this configuration, the secondary controller 50 may be configured to send data packets to the controller 24 that include configuration settings or calibration data.

In implementations where the second wireless data connection 58*b* is used for transmission of data packets between the controller 24 and the secondary controller 50, the controller 24 is configured to encode the electromagnetic waves 30 emitted by the distance sensor 18 with the data packets. The controller 24 may modulate either the amplitude or the frequency of the wavelength of the electromagnetic wave 30 to encode the data packet within the electromagnetic wave. The distance sensor 18 emits the encoded electromagnetic wave into the local environment 22 transmitting the data to the wireless communication module 56 or other receivers and devices configured to receive the encoded electromagnetic wave. The distance sensor 18 is also configured to receive an encoded electromagnetic wave from the wireless communication module 56 or other transmission source. The secondary controller 50 is configured to control the wireless communication module 56 to receive the encoded electromagnetic wave from the distance sensor 18 and read or process the data encoded therein. The secondary controller 50 may also be configured to encode the electromagnetic wave to be received by the distance sensor 18 with data. The signals communicated via the second wireless data connection 58*b* transmitted by the distance sensor 18 or the wireless communication module 56 may include the data packet encoded as characteristics in timing or amplitude of the wavelength being modulated. Whereas with the first wireless data connection 58*a*, the communication module 116 and the wireless communication module 56 emit repeated waveforms to transmit the data packet. Thus, the first and second wireless data connections 58*a* and 58*b* use different methods for transmitting the data packets between the controller 24 and the secondary controller 50. Additionally, in some implementations, the communication module 116 may be omitted and the distance sensor 18 or the wireless communication module 56 may be the sole means for wireless communication.

In various implementations, the data packet is communicated from the controller 24 to secondary controller 50 via the distance sensor 18, and the data packet is not communicated via the communication module 116 in addition to the distance sensor 18. In this configuration, the controller 24 and the secondary controller 50 may communicate similar or the same data packets as the first wireless connection 58*a* with or without the use the first wireless connection 58*a*. The monitoring device may forgo including the communication module 116 and using the first wireless data connection 58 as the second wireless data connection 58*b* may have an improved power consumption compared to the first wireless data connection 58*a*. The controller 24 may be configured to filter encoded electromagnetic waves emitted from the wireless communication module 56 from the determination of rate of the periodic biological movement of the user 14.

In some implementations, the controller 24 is configured to control the motion detection sensor 112. The motion detection sensor 112 may be an accelerometer, a gyroscope, a magnetometer, an inertial movement unit (IMU), an image-capturing device configured to sense motion, a combination of the listed or any other sensor or device configured to capture motion or a rate of motion. The motion detection sensor 112 may be configured to sense a movement of the user 14 or a user movement. The motion detection sensor 112 may sense an internal thoracic movement of the user and an external movement of the user 14. The magnitude of the movement sensed by the motion detection sensor 112 may be used by the controller 24 to determine whether the movement is the internal movement of the patient cavity 16 of the user 14 or a musculoskeletal movement of the user 14. For example, the external movement may be the user 14 moving from a laying position to a sitting position. The controller 24 may be configured to filter out the external movement of the user 14 from the determination of the periodic biological movement 12. By filtering the external movement of the user 14, the controller 24 may determine what change in distance sensed by the distance sensor 18 was effectuated by the movement of the patient cavity 16 of the user 14. The filtering of the external movement of the user 14 allows for the controller 24 to determine the rate of the periodic biological movement 12 during external movement of the user 14.

The controller 24 may be configured to compare the magnitude of movement sensed by the motion detection sensor 112 and a magnitude in the change in distance sensed by the distance sensor 18. For example, if a movement is reported by the distance sensor 18 but is not reported by the motion detection sensor 112, the controller 24 may filter or omit the corresponding motion data from being used to calculate the rate of the periodic biological movement 12. Alternatively, if significant motion is reported by the motion detection sensor 112 but is not reported by the distance sensor 18, the controller 24 may similarly filter the data from being utilized to calculate the rate of the periodic biological movement 12. In operation, the controller may filter the data based on a comparative analysis (e.g., a correlation) between the data reported by the distance sensor 18 and the data reported by the motion detection sensor 112. In the case of movement detected by either of the sensors 18 or 112 indicating motion in excess of a predetermined threshold, the motion data reported may be filtered from the results analyzed to calculate the rate of the periodic biological movement 12.

In general, the correlation between the magnitude of movement and the magnitude in the change in distance may be used to determine whether the change in distance was effectuated by the movement of the user 14 or the object 20 in the local environment 22. If the controller 24 determines there is a mismatch in magnitude of movement and magnitude of the change in distance, the controller 24 may filter the change in distance from the determination of the rate of the periodic biological movement 12. The correlation between the magnitudes of movement and the change in distance may also be used to determine a stationary reference object 20 in the local environment. For example, if a portion of the field of detection 40 of the distance sensor 18 is identified as being stationary based on the correlation, the corresponding portion of the field of detection 40 of the distance sensor 18 may be processed for the determination of the rate of the periodic biological movement 12. The remaining field of detection 40 may be filtered from the determination. The comparison of the motion data reported by the motion detection sensor 112 and the distance sensor 18 may allow the controller 24 to distinguish movements identified in the motion data and whether the movement should be attributed to the periodic biological movement 12 or other movements associated with the user 14 or the object 20.

The controller 24 may be configured to control the sensor suite 114. The sensor suite 114 may include optical sensors, sonar sensors, opacity sensors, thermal sensors, or any combination thereof. The sensor suite 114 may be config-ured to monitor or track variations of distance between the device 10 and the object 20. The variations of distance captured by the sensor suit 114 may be used by the controller 24 to filter or remove recorded variations in distance detected by the distance sensor 18 from the determination of the rate of the periodic biological movement 12. For example, if the sensor suite 114 includes an optical sensor, the controller 24 may be configured to determine when the object 20 is moving within an at least partially overlapping field of view of the optical sensor and the field of detection 40 of the distance sensor 18. The controller 24 may filter recorded variations in distance from the distance sensor 18 that corresponds with the movement of the object detected by the optical sensor from the determination of the rate of the periodic biological movement 12. The sensor suite 114 may also be configured to capture other patient information. For example, the thermal sensor may be configured to capture the external temperature of the user 14. The con-troller 24 may be configured to transmit the data and information connected to the secondary controller 50. The secondary controller 50 may be configured to log or process the information gathered from the sensor suite 114.

The controller 24 may also be configured to control the audio interface 118. The audio interface 118 may include a microphone and/or a speaker. The controller 24 may be configured to capture audio from the local environment 22. The controller 24 may determine when the user 14 is speaking based on the captured audio. The controller 24 may also filter changes in distance captured by the distance sensor 18 when the user 14 is talking. The controller may also emit an audio cue to alert the user 14 or another person in the local environment 22. The alert may be from the secondary controller 50 or to a condition set in the controller 24.

In some implementations, the biological monitoring device 10 may include the human machine interface (HMI) 120. The controller 24 may be configured to receive inputs from the HMI 120. The HMI 120 may include a plurality of operation controls, which may be configured as soft key, buttons, switches, similar tactile features, and/or combina-tions thereof. The plurality of operation controls may allow for the user 14 to select settings, operations, algorithms, programs, or other options stored on the memory 128 of the controller 24. The HMI 120 may also include a display. The controller 24 may be configured to display settings, opera-tions, algorithms, programs, or other options selected by the user 14 on the display. The controller 24 may also be configured to display the rate of the periodic biological movement 12.

The biological monitoring device 10 may include a power source 144. The power source 144 may be an integrated battery or battery pack within the housing 70. The power source 144 may be easily removable by being selectively attached within a recess of the housing 70. Alternatively, the battery may be disposed within the internal volume of the housing 70. The power source 144 may be re-chargeable and/or replaceable. The power source 144 may also be a power connecter to connect to a plug or power supply located in the local environment 22. The biological moni-toring device 10 may include either the battery or the power connector, or both the battery and the power connector. The power source 144 may provide power to the biological monitoring device 10.

Referring to FIG. 6, a method 200 of determining the rate of the periodic biological movement using the monitoring device 10 is illustrated. The method 200 may begin with step 202 where the electromagnetic wave 30 is emitted into the local environment 22. The electromagnetic wave 30 is emitted by the distance sensor 18 as instructed by the controller 24. The electromagnetic wave 30 is reflected off the object 20 in the local environment 22. Next, at step 204, the reflected electromagnetic wave 32 is sensed by the monitoring device 10. The distance sensor 18 is able to sense the reflected electromagnetic wave 32. At step 206, the change in distance between an origin of the electromagnetic wave emission and the object 20 in the local environment 22 is determined. The distance sensor 18, the origin of the electromagnetic wave emission, detects the distance between the monitoring device 10 and the object 20. The controller 24 is in communication with the distance sensor 18 and determines the change in distance between the monitoring device 10 and the object 20 based on the sensed distance. Next, in step 208, the rate of the periodic biological movement 12 is determined based on the change in distance between the origin of the electromagnetic wave emission and the object 20 in the local environment 22. The controller 24 determines the rate of the periodic biological movement 12 based on the change in distance between the origin of the electromagnetic wave, the distance sensor 18, and the object 20 in the local environment 22. The rate of the periodic biological movement 12 may be the respiration rate of the user 14 or the heart rate of the user 14.

The method 200 may include step 210 where the move-ment of the user 14 is sensed. The user movement may be sensed by the distance sensor 18 and/or by the motion detection sensor 112. Next, step 212 includes determining whether the sensed user or patient movement is the internal thoracic cavity movement or an external movement. The controller 24 may be configured to determine whether the patient's movement is the internal thoracic cavity movement or the external movement based on the sensed information from the distance sensor 18 and/or the motion detection sensor 112. When the distance sensor 18 is used to sense the movement of the user 14, the controller 24 may be config-ured to determine when a change in distance sensed is caused by the periodic biological movement 12 or caused by the external movement of the user 14. When the motion detection sensor 112 is used to sense the movement of the user 14, the controller 24 is configured to control the motion detection sensor 112 and receive the information sensed by the motion detection sensor 112. When both the motion detection sensor 112 and the distance sensor 18 are used to sense the movement of the user 14, the controller 24 may be configured to compare the change in distance and the sensed motion to determine whether the movement was caused by internal thoracic cavity movement or external body movement. Next, step 214 may include filtering the external movement from the determination of the rate of the periodic biological movement 12. The controller 24 may be configured to filter the change in distance caused by the external movement from the determination of the rate of the periodic biological movement 12.

The method 200 may further include step 216 determining whether the object 20 in the local environment 22 is static or non-static based on the change in distance between the origin of the electromagnetic wave emission and the object 20. The controller 24 may be configured to determine whether the object is static or non-static based on the change in distance detected by the distance sensor 18. Next, step 218 may include filtering the change in distance from the determination of the rate of the periodic biological movement 12 in response to the determination that the object 20 is non-static. The controller 24 may be configured to filter the change in distance caused by the object 20 being non-static from the determination of the rate of the periodic biological movement 12.

Step 220 may include embedding a data packet within the electromagnetic wave 30. The controller 24 may be configured to control the amplitude and/or frequency of the electromagnetic wave 30 to be emitted by the distance sensor 18 to embed the data packet therein. The data packet may include the rate of the periodic biological movement or other information sensed or received by the controller 24. The controller 24 communicates the data packet via the modulation of the wavelength of the electromagnetic wave 30.

For purposes of this disclosure, the terms "coupled" (in all of its forms: couple, coupling, coupled, etc.) and "connected" (in all of its forms: connect, connecting, connection, etc.) generally define the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connectors or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will become apparent to those skilled in the art that various modifications to the preferred embodiment of the invention as described herein can be made without departing from the spirit or scope of the invention as defined by the appended claims.

The invention claimed is:

1. A biological monitoring device, comprising:
a housing;
a distance sensor in connection with the housing, wherein the distance sensor is configured to emit an electromagnetic wave into a local environment and to sense the electromagnetic wave reflected off an object in the local environment and within a detection field of the distance sensor; and
a controller communicatively in connection with the distance sensor, wherein the controller is configured to:
control the distance sensor to emit the electromagnetic wave;
detect a change in distance between the biological monitoring device and the object based on the electromagnetic wave emitted by the distance sensor; and
determine a rate of a periodic biological movement based on the change of distance; and
modulate a wavelength of the electromagnetic wave to embed a data packet within the electromagnetic wave.

2. The biological monitoring device of claim 1, further comprising:
a motion detection sensor configured to sense a user movement.

3. The biological monitoring device of claim 2, wherein the controller is configured to:
determine whether the user movement sensed by the motion detection sensor is an internal thoracic cavity movement or an external body movement; and
filter the change in distance detected during the external body movement from the determination of the rate of the periodic biological movement.

4. The biological monitoring device of claim 2, wherein the controller is configured to:
determine whether the user movement sensed by the motion detection sensor is an internal thoracic cavity movement or an external body movement;
correlate a magnitude of the user movement sensed by the motion detection sensor and a magnitude of change in distance sensed by the distance sensor in response to determination that the user movement is the internal thoracic cavity movement;
determine whether the object is static or non-static based on the correlation between the magnitude of movement and the magnitude of change in distance; and
filter the change in distance from the determination of the rate of the periodic biological movement in response to the determination that the object is non-static.

5. The biological monitoring device of claim 1, wherein the data packet includes the rate of the periodic biological movement.

6. The biological monitoring device of claim 1, wherein the rate of the periodic biological movement is one of a heart rate or a respiration rate.

7. The biological monitoring device of claim 1, wherein a data packet is not communicated via a communication module in addition to the distance sensor.

8. The biological monitoring device of claim 1, wherein the distance sensor is a phased array having at least one transmitter element and a plurality of sensor elements, and wherein the at least one transmitter element is configured to emit the electromagnetic wave and each sensor element of the plurality of sensor elements is configured to sense the electromagnetic wave reflected off the object.

9. The biological monitoring device of claim 1, wherein the controller is configured to:

control the at least one transmitter element to emit the electromagnetic wave; and compare the change in distance between the biological monitoring device and the object based on the electromagnetic wave emitted by the at least one transmitter element.

10. The biological monitoring device of claim 1, where in the controller is configured to:

determine whether the object is static or non-static based on the change in distance between the biological monitoring device and the object; and filter the change in distance from the determination of the rate of the periodic biological movement in response to the determination that the object is non-static.

11. A method for monitoring a periodic biological movement, comprising:

emitting an electromagnetic wave into a local environment;

sensing the electromagnetic wave reflected off an object located in the local environment;

detecting a change in distance between an origin of the electromagnetic wave emission and the object in the local environment based on the electromagnetic wave;

determining whether the object located in the local environment is static or non-static based on the change in distance be ween the origin of the electromagnetic wave emission and the object;

determining a rate of the periodic biological movement based on the change in distance between the origin of the electromagnetic wave emission and the object; and filtering the change in distance from the determination of the rate of the periodic biological movement in response to the determination that the object is non-static.

12. The method of claim 11, further comprising:

sensing a patient movement;

determining whether the patient movement sensed is an internal thoracic cavity movement or an external body movement; and filtering the change in distance detected during the external body movement from determining the rate of the periodic biological movement.

13. The method of claim 11, further comprising:

communicating a data packet via a modulation of a wavelength of the electromagnetic wave, wherein the data packet includes the rate of the periodic biological movement.

14. A monitoring system for a patient, comprising:

a housing;

a distance sensor in connection with the housing, wherein the distance sensor is configured to emit an electromagnetic wave into a local environment away from the patient and to sense the electromagnetic wave reflected off an object in the local environment and within a detection field of the distance sensor; and a first controller communicatively in connection with the distance sensor, wherein the first controller is configured to:

control the distance sensor to emit the electromagnetic wave;

detect a change in distance between the distance sensor and the object based on the electromagnetic wave emitted by the distance sensor; and determine a rate of a periodic biological movement of the patient based on the change of distance.

15. The patient monitoring system of claim 14, wherein the second controller is configured to monitor the rate of the periodic biological movement relative to a range of stored rates.

16. The patient monitoring system of claim 14, wherein the second controller is configured to store the data packet in a patient medical file.

17. The patient monitoring system of claim 14, wherein the data packet includes the rate of the periodic biological movement, and wherein the second controller is configured to display the periodic biological movement on a display device in communication with the second controller.

18. The patient monitoring system of claim 14, wherein the housing is configured to be worn by a user, and wherein the distance sensor is configured to emit the electromagnetic wave along an emission axis oriented away from the patient.

19. The patient monitoring system of claim 14, wherein the controller is further configured to:

identify the periodic biological movement as being attributed to an internal thoracic cavity and filtering nonconforming movements attributed to the movement of the object or an external body movement of the patient.

20. The patient monitoring system of claim 14, wherein the object in the local environment is fixed over a monitoring period of the periodic biological movements.

* * * * *